(12) United States Patent
Palepu

(10) Patent No.: US 6,743,414 B2
(45) Date of Patent: Jun. 1, 2004

(54) INHALATION ADMINISTRATION OF BIOPHOSPHONATES

(75) Inventor: Nageswara R. Palepu, Mill Creek, WA (US)

(73) Assignee: Geneva Pharmaceuticals, Inc., Princeton, NJ (US)

(*) Notice: Subject to any disclaimer, the term of this patent is extended or adjusted under 35 U.S.C. 154(b) by 103 days.

(21) Appl. No.: 10/150,713

(22) Filed: May 17, 2002

(65) Prior Publication Data

US 2003/0064966 A1 Apr. 3, 2003

Related U.S. Application Data

(63) Continuation-in-part of application No. 09/847,827, filed on May 2, 2001, now abandoned.

(51) Int. Cl.[7] .............................. A61K 9/12; A61K 9/72; A61K 31/41
(52) U.S. Cl. ...................... 424/45; 424/482; 424/185.1; 514/89; 514/416; 514/384; 514/172; 514/174
(58) Field of Search ....................... 424/45, 482, 185.1; 514/89, 384, 416, 172, 174

(56) References Cited

U.S. PATENT DOCUMENTS

| 5,183,815 | A | * | 2/1993 | Saari et al. | ................. 514/172 |
| 5,661,174 | A | * | 8/1997 | Naumann et al. | ........... 514/416 |
| 6,143,326 | A | * | 11/2000 | Mockel et al. | ............... 424/482 |
| 6,414,006 | B1 | * | 7/2002 | Harada et al. | ............... 514/384 |
| 6,482,411 | B1 | * | 11/2002 | Ahuja et al. | ............. 424/185.1 |

FOREIGN PATENT DOCUMENTS

| DE | WO 0000182 | * | 1/2000 |

OTHER PUBLICATIONS

Physicians' Desk Reference, Drug Information on Fosamax® (Merck), 1995. (obtained through on–line PDR).*
The Bantam Medical Dictionary, (Laurence Urdang Associates Ltd.), 1982, pp. 212 and 358.*
Remington: The Practice of Science and Pharmacy, 19th edition, Chapt. 41, pp. 710–712 (1995).
J. L. McGuire (editor), Pharmaceuticals, vol. 4, pp. 2084–2085 (2000).

* cited by examiner

*Primary Examiner*—Michael G. Hartley
*Assistant Examiner*—M. Haghighatian
(74) *Attorney, Agent, or Firm*—Lydia T. McNally

(57) ABSTRACT

The present invention relates to the treatment and prevention of bone diseases in humans, including osteoporosis in postmenopausal women, Paget's Disease and hypercalcemia, by administration of a bisphosphonate in an inhalation form. The invention also relates to pharmaceutical inhalation compositions suitable for the treatment and prevention of bone diseases.

6 Claims, 4 Drawing Sheets

NOTE: DASHED LINES AT BOTTOM OF EACH PLOT ARE FROM ANIMALS 11, 14, AND 16 WHICH WERE EXCLUDED FROM CALCULATION OF MEAN PHARMACOKINETIC PARAMETER VALUES.

INHALATION ADMINISTRATION OF BIOPHOSPHONATES

This application is a continuation-in-part of U.S. application Ser. No. 09/847,827, filed May 2, 2001 now abandoned.

FIELD OF THE INVENTION

The present invention relates to the treatment and prevention of bone diseases in humans, including osteoporosis in postmenopausal women, Paget's Disease and hypercalcemia, by administration of a bisphosphonate in an inhalation form. The invention also relates to pharmaceutical inhalation compositions suitable for the treatment and prevention of bone diseases.

BACKGROUND OF THE INVENTION

Bisphosphonates are known in the art as bone resorption inhibitors. Examples of bisphosphonates include, alendronate, 4-amino-1-hydroxybutylidene-1,1-bisphosphonic acid; tiludronate, 4-chlorophenylthiomethylene bisphosphonatic acid; pamidronate, (3-amino-hydroxypropylidnen) bisphosphonic acid; etidronate, (1-hydroxyethylidene)bisphosphonic acid; residronate, 1-hydroxy-2-(3-pyridinyl)ethylidene bisphosphonic acid; zoledronate, 2-(imidazol-1-yl)-1-hydroxyethane-1,1-bisphosphonic acid; and the pharmaceutically acceptable salts of the above compounds.

Bisphosphonates, and their pharmaceutically acceptable salts, are useful in the treatment and prevention of bone diseases such as osteoporosis. Specifically, bisphosphonates are useful for the treatment of urolithiasis and are capable of inhibiting bone reabsorption. Bisphosphonates are also useful in lessening the risk of non-vertebral fractures in osteoporotic women and as a therapeutic agent for hypercalcemia and Paget's disease.

Current treatments for the above conditions comprise administration of a pharmaceutically effective amount of a bisphosphonic acid in oral dosage forms such as tablets. Bisphosphonates may also be administered by intravenous methods. The benefits of bisphosphonates are observed by its effect on bone mass and density. However oral and intravenous dosage forms have very low bioavailability. In some instances, the bioavailability is less than 1%. Accordingly, it would be desirable to find a route of administration of bisphosphonates that substantially increases its bioavailability.

In addition, oral dosage forms of the free acid form of certain bisphosphonates, e.g. 4-amino-1-hydroxybutylidene-1,1-bisphosphonic acid, may result in gastric irritability, and therefore it would also be desirable to administer these bisphosphonates by a route that avoids such gastrointestinal problems.

DESCRIPTION OF THE INVENTION

Figure 1:
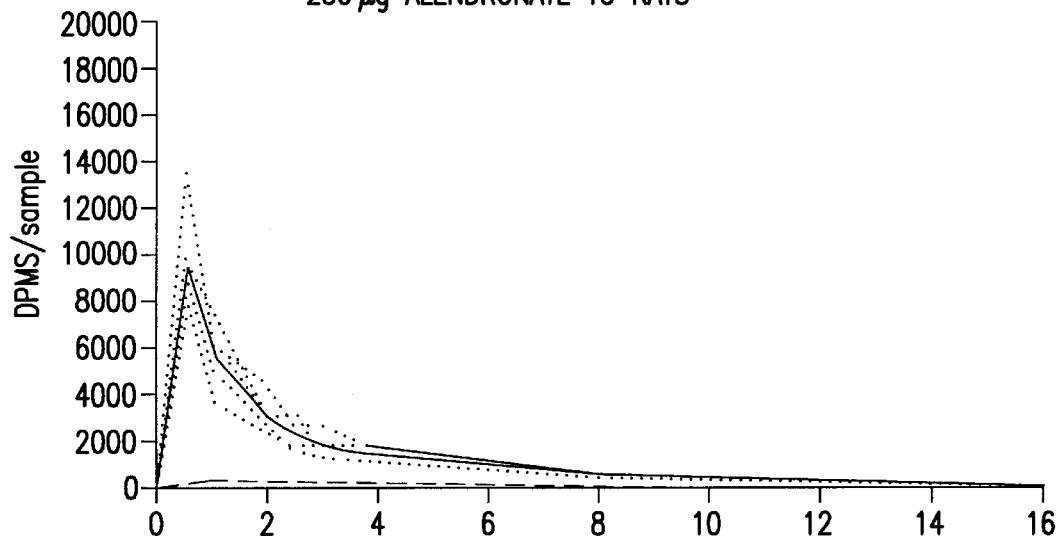
FIG. 1 shows a plot of Plasma disintegrations per minute ("DPM") following intratracheal administration of 250 μg if alendronate to rats.
Figure 1:
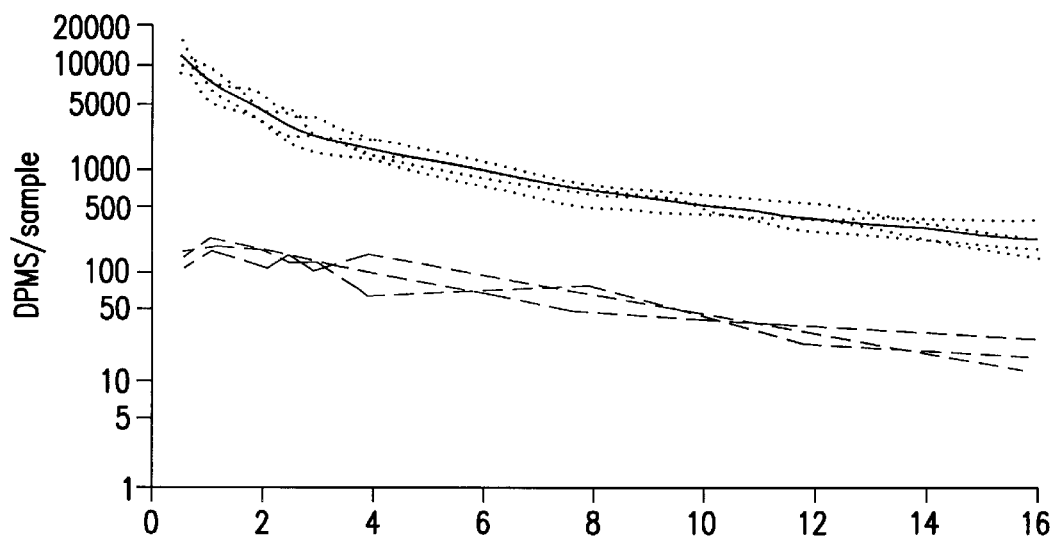

It has been found, in accordance with the present invention, that administration of a pharmaceutically effective dose of a bisphosphonic acid, or its pharmaceutically acceptable salts, through inhalation directly into the respiratory tract, produces much higher bioavailability than via oral or intravenous administration and avoids the gastrointestinal problems associated with oral dosage forms of bisphosphonates.

Accordingly, the present invention relates to the treatment and prevention of osteoporosis in postmenopausal women, and the treatment of urolithiasis and the inhibition of bone reabsorption, by administration of a bisphosphonate in an inhalation form. The invention also relates to inhalation compositions suitable for the treatment of and prevention of osteoporosis in postmenopausal women, and the treatment of urolithiasis and the inhibition of bone reabsorption.

Examples of bisphosphonates of the present invention include alendronate, 4-amino-1-hydroxybutylidene-1,1-bisphosphonic acid; tiludronate, 4-chlorophenyl thiomethylene bisphosphonatic acid; pamidronate, (3-amino-hydroxypropylidnen) bisphosphonic acid; etidronate, (1-hydroxyethylidene)bisphosphonic acid; residronate, 1-hydroxy-2-(3-pyridinyl)ethylidene bisphosphonic acid; zoledronate, 2-(imidazol-1-yl)-1-hydroxyethane-1,1-bisphosphonic acid; and the pharmaceutically acceptable salts of the above compounds.

The pharmaceutically acceptable salts of the above bisphosphonic acids include salts of alkali metals (e.g., Na, K), alkali earth metals (e.g., Ca), salts of inorganic acids, such as HCl and salts of organic acids such as citric acid and amino acids. Sodium salt forms are preferred. When alendronate is used, the monosodium salt trihydrate form is most preferred. In an alternative embodiment, alendronate may be administered in its anhydrous form.

Bisphosphonate formulations of the present invention are administered in an inhalation dosage form directly into the respiratory tract. Bisphosphonate compounds may be administered by any of the methods and formulations employed in the art for inhalation administration. Such methods include metered dose, nebulizers, breath activated or powder.

In one embodiment, the route of administration is in a powder form. The active ingredient may be used as a powder with a particle size of 1 to 10 micrometers, preferably 2–8 micrometers. For pharmaceutical purposes the particle size of the powder should desirably be no greater than 100 microns diameter, since larger particles may clog the valve or orifice of the container. Preferably the particle size of the finely-divided solid powder should for physiological reasons be less than 25 microns and preferably less than about 10 microns in diameter. The particle size of the powder for inhalation therapy should most preferably be in the range of 2 to 10 microns.

There is no lower limit on particle size except that imposed by the intended use of the produced. Where the powder is a solid medicament, the lower limit of particle size is that which will be readily absorbed and retained on or in body tissues. When particles of less than about one-half micron in diameter are administered by inhalation they tend to be exhaled by the patient.

The concentration of medicament depends upon the desired dosage but is generally in the range 0.01 to 5% by weight. A preferred dosage in inhalation form would be 50–100 micrograms per day and administration of the inhalation composition would be on a once a day or once a week schedule. However the precise therapeutic dosage amount will depend on the age, size, sex and condition of the subject, the nature and severity of the disorder, and other such factors. An ordinarily skilled physician or clinician can readily determine and prescribe the effective amount of the drug required for a particular patient.

Other embodiments of the present invention include powdered aerosol formulations which comprise the active ingredient suspended or dispersed in a propellant or a propellant and solvent.

The propellant generally comprises a mixture of liquified chlorofluorocarbons (CFCs) which are selected to provide the desired vapor pressure and stability of the formulation. Propellants 11, 12 and 114 are the most widely used propellants in aerosol formulations for inhalation administration. Other commonly used propellants include Propellants 113, 142b, 152a 124, and dimethyl ether. The compound 1,1,1,2-tetrafluoroethane is also a commonly used propellant for medicinal aerosol formulations. The propellant comprises 40 to 90% by weight of the total inhalation composition.

The inhalation composition may also contain dispersing agents and solvents, such as methylene chloride, ethanol or phosphate buffer solution (PBS). Surfactants have also been used as dispersing agents. Such agents include sorbitan tiroleate, oleyl alcohol, oleic acid, lecithin or oils derived from natural sources, such as, corn oil, olive oil, cotton seed oil and sunflower seed oil are useful in keeping the suspended particles form agglomerating. The surface active agents are generally present in amounts not exceeding 5 percent by weight of the total formulation. They will usually be present in the weight ratio 1:100 to 10:1 surface active agent to bisphosphonate, but the surface active agent may exceed this weight ratio in cases where the drug concentration in the formulation is very low.

The powder inhalation composition of this embodiment of the present invention may also comprise a lubricant such as isopropyl myristate, light mineral oil or other substances which provide slippage between particles of the compound as well as lubrication for component parts of the valve of the inhalation device.

The inhalation formulation of the present invention can be delivered in any conventional inhalation device employed in the art for the administration of a medicinal compound.

In alternative embodiments, the bisphosphonate can be administered into the respiratory tract by any inhalation form known in the art.

In the methods and compositions of the present invention, the active ingredient is typically administered in admixture with suitable pharmaceutical diluents, excipients or carriers. Moreover, when desired or necessary, suitable binders, lubricants, disintegrating agents and coloring agents can also be incorporated into the mixture of active ingredient(s) and inert carrier materials. Suitable binders may include starch, gelatin, natural sugars such as glucose, anhydrous lactose, free-flow lactose, beta-lactose, and corn sweeteners, natural and synthetic gums, such as acacia, tragacanth or sodium alginate, carboxymethyl cellulose, polyethylene glycol, waxes, cross carmallose sodium, and the like. Lubricants used in these dosage forms include sodium oleate, sodium stearate, magnesium stearate, sodium benzoate, sodium acetate, sodium chloride and the like.

When using an inhalation device, the drug that does not go to the lungs will eventually reach the stomach. Where it will be converted into an acid form. The acid form of alendronate is known to have severe esophageal toxicities. To avoid this, alendronate particles can be coated with an enteric coated polymer so that the drug will not be released until it reaches the small intestine. Once the drug is released in the small intestine, it will not return to the esophagus during the reflux reaction. In an alternative embodiment of the present invention, the active ingredient, alendronate, can be coated with enteric polymers including sureteric, cellulose acetate phthalate, methacrylic acid copolymer, hydroxypropyl methylcellulose phthalate, aquacoat ECD 30, shellac and zein.

The invention will now be illustrated by the following Examples, which are merely illustrative and not intended to limit the scope of the present invention.

EXAMPLES $^{14}$C-alendronate sodium is obtained from Chemsyn Science Laboratories and stored frozen at $-80°$ C. Prior to use, the solution is diluted using PBS to make a dosing solution.

Sprague-Dawley rats with jugular and femoral vein catheters from Hilltop (Scottsdale, Pittsburgh, Pa.) are used. Each rat weighs between 250–300 grams.

Example 1

In this example the pharmacokinetic parameters following intratracheal (i.t.) and intravenous (i.v.) doses of $^{14}$C-alendronate are evaluated. Sixteen rats (N=8/group, 4 males and 4 females/group) were randomly chosen and divided into two groups. Rats will receive an i.t. and i.v. dose of $^{14}$C-alendronate, 250 µg (24.5 µCi/animal). Blood samples (~0.15 mL) are collected from the jugular or cephalic vein at predose (2 to 0.25 hours prior to dosing), 0.5, 1, 2, 2.5, 3, 4, 8, 12 and 16 hours postdose for both groups. The whole blood samples are stored frozen at approximately $-20°$ C. until analyzed by counting radioactivity by a liquid scintillation procedure.

TABLE 1

Group Assignments

| Group No. | Test Article/Route of Administration | Number of Animals/ Gender | Total Daily Dose (µg/animal) | Dosing Days |
|---|---|---|---|---|
| 1 | $^{14}$C-alendronate/i.t. | 4/M & 4/F | 250 µg/animal (24.5 µCi/animal) | 1 |
| 2 | $^{14}$C-alendronate/i.v. | 4/M & 4/F | 250 µg/animal (24.5 µCi/animal) | 1 |

Each rat in the i.t. dose group is anesthetized for about 5 minutes with isoflurane anesthetic (oxygen with 3.0 to 5.0% isoflurane). Each rat is vertically held by hanging its upper jaw to a rubber band which is stretched using two burette stands. The i.t. dose is administered by a blunt stainless steel needle for intratracheal instillation with a gavage needle inserted in through the mouth into the trachea just above the main carina.

The rats in the i.v. group receive similar anesthesia treatment.

TABLE 2

Dose levels

| Group No. | Test Article/Route of Administration | Total Daily Dose (μg/animal) | Dose Volume (ml/animal) | Dose Concentration ((μg/ml) |
|---|---|---|---|---|
| 1 | ¹⁴C-alendronate/i.t. | 250 μg/animal (24.5 μCi/animal) | 0.30 | 833 |
| 2 | ¹⁴C-alendronate/i.v. | 250 μg/animal (24.5 μCi/animal) | 0.30a | 833 |

Blood samples are collected from the jugular or cephalic vein at predose (2 to 0.25 hours prior to dosing), 0.5, 1, 2, 2.5, 3, 4, 8, 12 and 16 hours postdose for both groups. The samples are analyzed for $^{14}$C-alendronate in a scintillation counter to determine the maximum blood concentration ($C_{MAX}$), time to maximum blood concentration ($T_{MAX}$), area under the blood concentration vs. time curve (AUC), and terminal half-life ($t_{1/2}$). The results are shown below in Table 3.

TABLE 3

Pharmacokinetics of Alendronate following Intratracheal (IT) and Intravenous (IV) Administration to Rats

| Parameter | N[a] | IT Administration Mean | SD | N | IV Administration Mean | SD | IV Administration Ratio IT/IV |
|---|---|---|---|---|---|---|---|
| $C_{max}$ (DPM/sample) | 5 | 9501 | 2519 | 8 | NA | NA | NA |
| $T_{max}$ (hr) | 5 | 0.5 | 0 | 8 | NA | NA | NA |
| AUC(0–∞) (DPM/sample*Hr) | 5 | 22503 | 4065 | 8 | 19820 | 18830 | 1.14[b] |
| $t_{1/2}$ Lambda z (hr) | 5 | 5.28 | 2.94 | 8 | 6.3 | 2.47 | 0.84 |

Notes:
NA = Not applicable
$C_{max}$ = Maximum observed plasma concentration
$T_{max}$ = Time of Cmax
AUC(0–∞) = Area under the plasma concentration time curve extrapolated to infinite time
$t_{1/2}$ Lambda z = Half-life associated with apparent terminal elimination rate constant The mean $C_{MAX}$ of alendronate following i.t. administration was 9501 DPM/sample with a mean $T_{MAX}$ of 0.5 hours. The bioavailability of the i.t. dose relative to the i.v. dose of alendronate was 114%.

Figure 2:
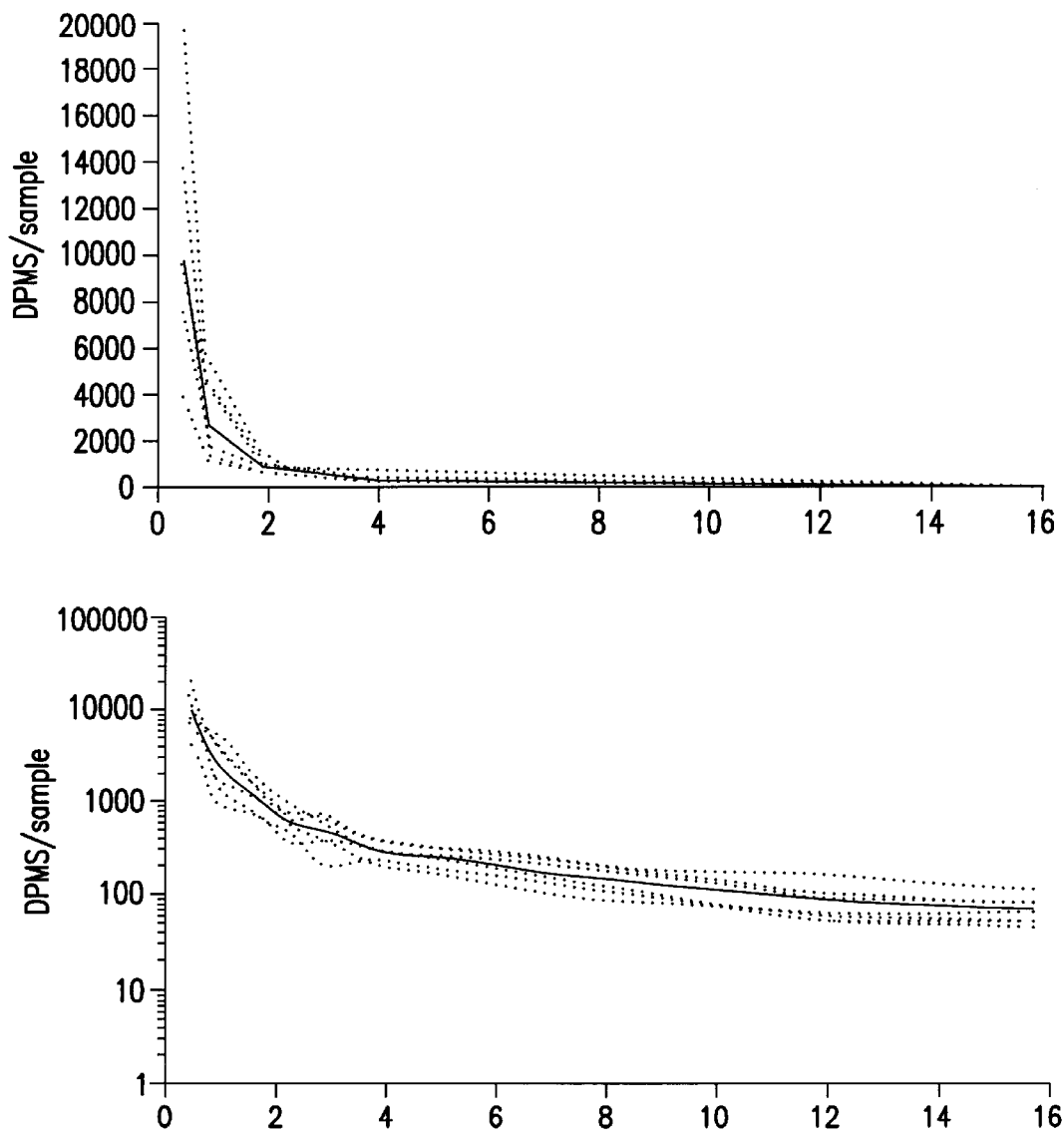
FIG. 2 shows a plot of Plasma disintegrations per minute ("DPM") following intravenous administration of 250 μg if alendronate to rats.

Plasma concentrations verses time are shown in FIGS. 1 and 2. Three of the rates in the i.t. group did not receive the dose to the lung, but rather to the stomach; the results for these rats is shown as the dashed line at the bottom of FIG. 1.

The data in FIGS. 1 and 2 show that alendronate is rapidly and completely absorbed from the lungs. Therefore the bioavailability of alendronate administered directly to the lungs is expected to be 100%. However, the amount of drug that can be delivered to the lungs using an inhalation device varies 30–70%.

Example 2

In the following example, alendronate was coated with Eudragit L-30D-55, an enteric polymer comprising methacrylic acid copolymer. The following formulations were prepared:

| | |
|---|---|
| I: Uncoated Alendronate beads | |
| Nu-Parelis (Sugar Spheres) 20/25 mesh | 868.055 mg/g |
| Alendronate sodium | 47.454* mg/g |
| Povidone | 70.602 mg/g |
| Talc | 13.889 mg/g |
| Purified water | removed |
| II: Alendronate coated beads | |
| Alendronate beads Form I | 754.955 mg/g |
| Eudragit L-30D-55 | 181.129 mg/g |
| Talc | 36.383 mg/g |
| Triethyl Citrate | 27.533 mg/g |
| Purified water | removed |

(*equivalent to 36.363 mg/g alendronate)

Uncoated alendronate beads were prepared by dissolving povidone and alendronate sodium in purified water. Talc was suspended in purified water and the solution and suspension were combined. The povidone, alendronate sodium and talc suspension were sprayed onto the Nu-Parelis. The uncoated alendronate beads were screened.

To prepare the alendronate coated beads, Eudragit and triethyl citrate were combined to form a suspension. Talc and purified water were combined to form a second suspension; and the two suspensions were combined. The Eudragit, triethyl citrate and talc suspensions sprayed onto the uncoated alendronate beads. The finished coated beads were screened.

Figure 3:
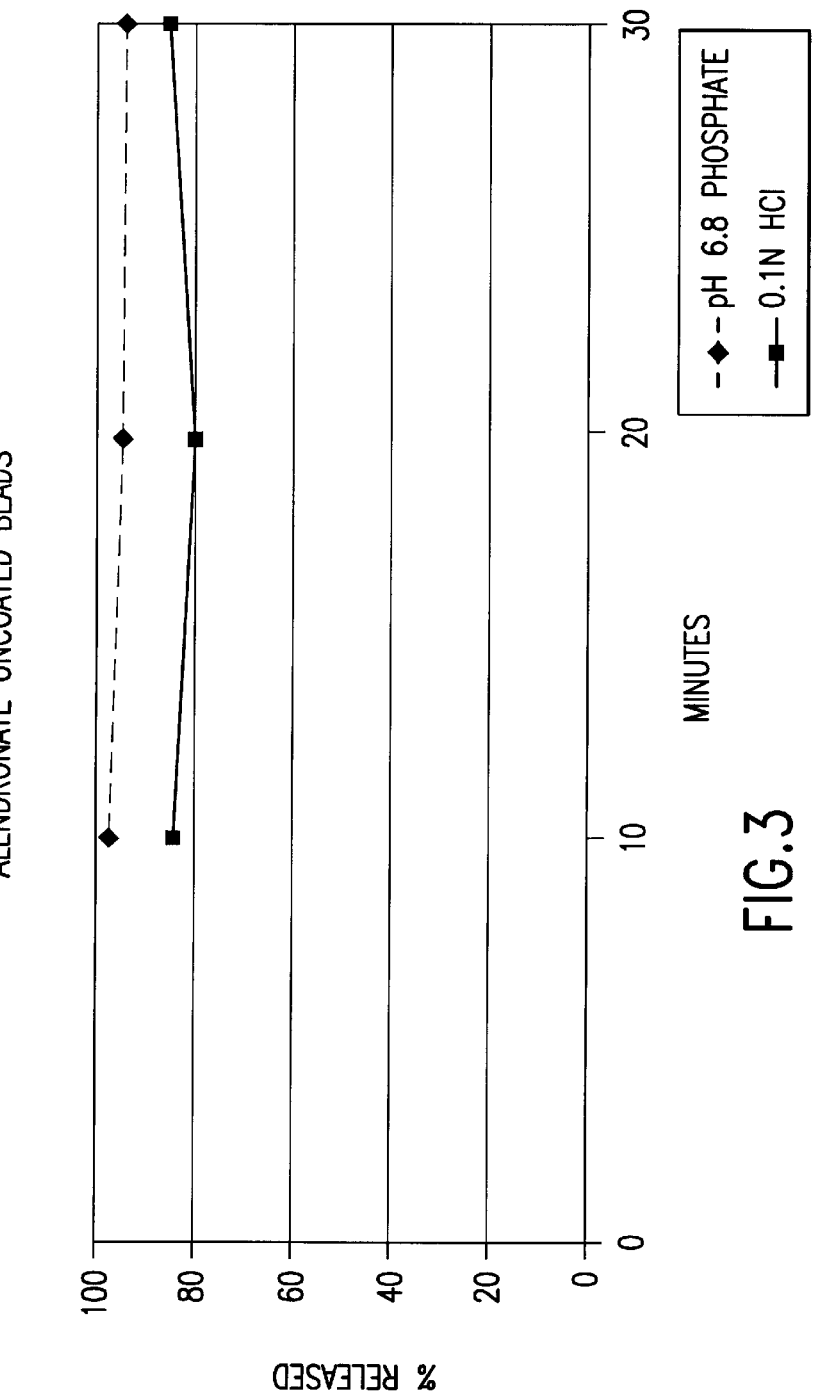
FIG. 3 shows the percent drug release verses time in pH 6.8 phosphate and 0.1 N HCl for alendronate beads.
Figure 4:
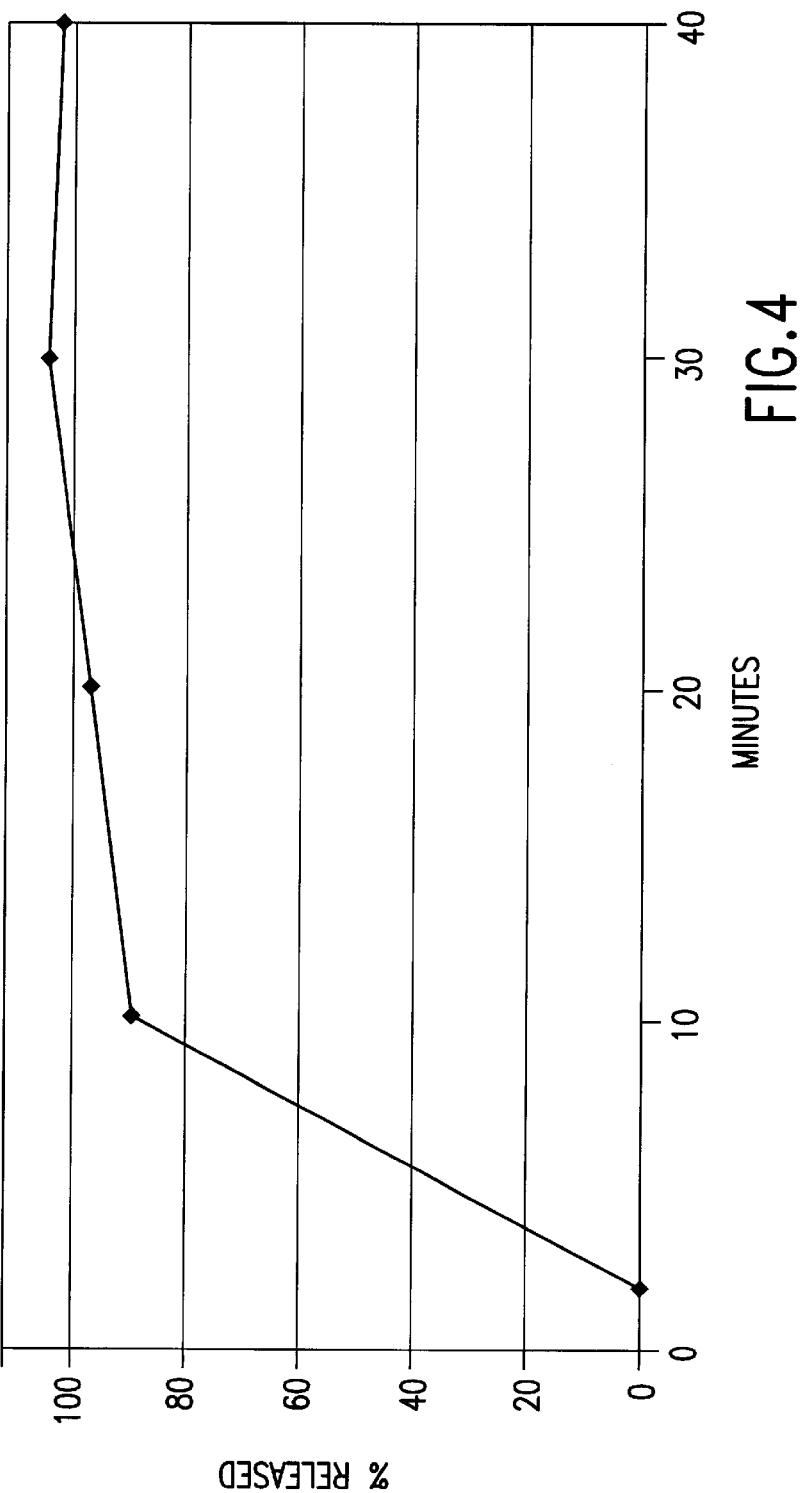
FIG. 4 shows the percent drug release verses time in pH 6.8 phosphate and 0.1 N HCl for alendronate beads coated with an enteric polymer.

The finished alendronate enteric coated beads along with uncoated beads were tested for dissolution as a function of time. The dissolution results showed that the uncoated alendronate beads released in 0.1 N HCl and in pH 6.8 phosphate buffer. The enteric coated alendronate beads had no drug release for 2 hours in 0.1 N HCl and showed similar drug release to the uncoated beads in pH 6.8 phosphate buffer. Graphs of the dissolution testing can be found in the FIGS. 3 and 4. The results show that alendronate can be enteric coated so that drug release is stopped in 0.1 N HCl and then released in pH 6.8 phosphate buffer.

What is claimed is:

1. A method for treating or preventing bone resorption in a human in need thereof consisting essentially of administering to the lungs of said human a therapeutically effective amount of a bisphosphonic acid, its pharmaceutically acceptable salts, or mixtures thereof.

2. A method for the treatment and prevention of osteoporosis in postmenopausal women consisting essentially of administering to the lungs of a therapeutically effective amount of a bisphosphonic acid, its pharmaceutically acceptable salts, or mixtures thereof.

3. A method for treating or preventing bone resorption in a human in need thereof according to claim 1 wherein the bisphosphonic acid is selected from the group consisting of alendronate, 4-amino-1-hydroxybutylidene-1,1-bisphosphonic acid; tiludronate, 4-chlorophenylthiomethylene bisphosphonatic acid; pamidronate, (3-amino-hydroxypropylidnen) bisphosphonic acid; etidronate, (1-hydroxy ethylidene) bisphosphonic acid; residronate, 1-hydroxy-2-(3-pyridinyl)ethylidene bisphosphonic acid; zoledronate, 2-(imidazol-1-yl)-1-hydroxyethane-1,1-bisphosphonic acid; and the pharmaceutically acceptable salts of the above compounds.

4. A method for treating or preventing bone resorption in a human in need thereof according to claim 1 wherein the bisphosphonic acid is alendronate, 4-amino-1-hydroxybutylidene-1,1-bisphosphonic acid, its pharmaceutically acceptable salts and mixtures thereof.

5. A method for the treatment and prevention of osteoporosis in postmenopausal women according to claim 2 wherein the bisphosphonic acid is selected from the group consisting of alendronate, 4-amino-1-hydroxybutylidene-1,1-bisphosphonic acid; tiludronate, 4-chlorophenylthiomethylene bisphosphonatic acid; pamidronate, (3-amino-hydroxypropylidnen) bisphosphonic acid; etidronate, (1-hydroxy ethylidene) bisphosphonic acid; residronate, 1-hydroxy-2-(3-pyridinyl)ethylidene bisphosphonic acid;

zoledronate, 2-(imidazol-1-yl)-1-hydroxyethane-1,1-bisphosphonic acid; and the pharmaceutically acceptable salts of the above compounds.

6. A method for the treatment and prevention of osteoporosis in postmenopausal women according to claim 2 wherein the bisphosphonic acid is alendronate, 4-amino-1-hydroxybutylidene-1,1-bisphosphonic acid, its pharmaceutically acceptable salts and mixtures thereof.

* * * * *

UNITED STATES PATENT AND TRADEMARK OFFICE
CERTIFICATE OF CORRECTION

PATENT NO. : 6,743,414 B2  
DATED : June 1, 2004  
INVENTOR(S) : Nageswara R. Palepu It is certified that error appears in the above-identified patent and that said Letters Patent is hereby corrected as shown below:

<u>Title page,</u>  
Item [*] Notice, should read -- Notice: Subject to any disclaimer, the term of this patent is extended or adjusted under 35 U.S.C. 154(b) by 0 days. --

Signed and Sealed this

Nineteenth Day of April, 2005

JON W. DUDAS  
*Director of the United States Patent and Trademark Office*